United States Patent [19]

Clark et al.

[11] 4,448,787
[45] May 15, 1984

[54] 6-SUBSTITUTED PYRANONE COMPOUNDS AND THEIR USE AS PHARMACEUTICALS

[75] Inventors: Barry P. Clark, Fleet; William J. Ross, Lightwater; Alec Todd, Wokingham, all of England

[73] Assignee: Lilly Industries Limited, London, England

[21] Appl. No.: 303,297

[22] Filed: Sep. 17, 1981

Related U.S. Application Data

[62] Division of Ser. No. 134,135, Mar. 27, 1981, Pat. No. 4,304,728.

[30] Foreign Application Priority Data

Apr. 5, 1979 [GB] United Kingdom ................ 7912062

[51] Int. Cl.$^3$ .............................................. A61K 31/35
[52] U.S. Cl. ..................................... 424/283; 424/269
[58] Field of Search ................ 260/345.7 R; 424/283, 424/269; 542/453, 454, 459; 548/252, 253; 549/416, 420

[56] References Cited

U.S. PATENT DOCUMENTS 4,060,533 11/1977 Nadelson ...................... 260/345.7 R
4,065,290 12/1977 Taylor ............................. 564/345 X

OTHER PUBLICATIONS

Borsche et al., Ann, 453, 148, (1927).
Soliman et al., J. Chem. Soc., 1956, pp. 3663–3668.
Eiden et al., Arch. Pharm., 308, 489 (1975).
Schiefer et al., Angew. Chem. Internat. Edit., 4, 527 (1965).
Kirby et al., J. Org. Chem., 28, 2266 (1963).
Hampton et al., J. Org. Chem., 30, 4263 (1965).
Garkusha, Chem. Abstract, 63, 1458d (1965).

*Primary Examiner*—Nicky Chan
*Attorney, Agent, or Firm*—Karen B. Dow; Arthur R. Whale

[57] ABSTRACT

Compounds are described of the formula

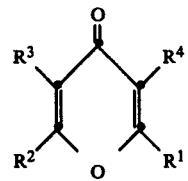

in which $R^1$ is $COOR^5$, $CONHR^5$, cyano, 5-tetrazolyl or $R^6$, where $R^5$ is hydrogen or $C_{1-8}$ alkyl and $R^6$ is phenyl or naphthyl, the phenyl or naphthyl group being optionally substituted by one or more group selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$ and $SR^5$; $R^2$ is $R^6$ or $-CH=CH-R^6$ when $R^1$ is $COOR^5$, $CONHR^5$, cyano or 5-tetrazolyl, or $R^2$ is $-CH=CH-R^6$ when $R^1$ is $R^6$; $R^3$ is hydrogen, $C_{1-6}$ alkyl, halogen, hydroxy or $-OCH_2R^6$; and $R^4$ is hydrogen, $C_{1-6}$ alkyl or halogen; and salts thereof. The compounds have pharmaceutical properties and in particular are useful in the treatment of immediate hypersensitivity conditions such as asthma.

6 Claims, No Drawings

6-SUBSTITUTED PYRANONE COMPOUNDS AND THEIR USE AS PHARMACEUTICALS

This application is a division, of application Ser. No. 134,385, filed Mar. 27, 1981 now U.S. Pat. No. 4,304,728.

This invention relates to pyranone compounds and their use as pharmaceuticals.

Certain pyran-4-one compounds have already been described in the literature and, for example, compounds of this type are disclosed in Annalen 453, 148(1927), J.Chem.Soc. 3663(1956), Arch.Pharm. 308, 489 (1975), Angew.Chem. Internat. Edit. 4,527(1965) and in J.Org.-Chem.28, 2266 (1963) and 30, 4263 (1965). However, the pharmaceutical properties of the compounds were not investigated and in no instance was any useful biological activity attributed to the compounds.

We have now discovered certain novel pyran-4-one compounds and the broad utility of the compounds as pharmaceuticals, especially in the treatment of immediate hypersensitivity conditions.

The invention comprises a compound of formula (I)

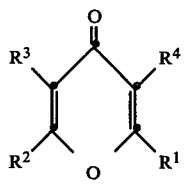

in which $R^1$ is $COOR^5$, $CONHR^5$, cyano, 5-tetrazolyl or $R^6$, where $R^5$ is hydrogen or $C_{1-8}$ alkyl and $R^6$ is phenyl or naphthyl, the phenyl or naphthyl being optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$ and $SR^5$; $R^2$ is $R^6$ or $-CH=CH-R^6$ when $R^1$ is $COOR^5$, $CONHR^5$, cyano or 5-tetrazolyl, or $R^2$ is $-CH=CH-R^6$ when $R^1$ is $R^6$; $R^3$ is hydrogen, $C_{1-6}$ alkyl, halogen, hydroxy or $-OCH_2R^6$; and $R^4$ is hydrogen, $C_{1-6}$ alkyl or halogen; and salts thereof; provided that (i) when $R^3$ is hydrogen, $R^4$ is hydrogen or methyl and $R^1$ is $COOR^5$ or $CONHR^5$ where $R^5$ is hydrogen, methyl or ethyl, $R^2$ is not phenyl, (ii) when $R^3$ and $R^4$ are both hydrogen and $R^1$ is $COOR^5$ where $R^5$ is methyl, $R^2$ is not 2-methoxyphenyl or 4-methoxyphenyl (iii) when $R^3$ and $R^4$ are both hydrogen and $R^1$ is $COOR^5$ where $R^5$ is ethyl, $R^2$ is not 3,4-dimethoxyphenyl, and (iv) when $R^3$ and $R^4$ are both hydrogen and $R^1$ is phenyl or 4-methoxyphenyl, $R^2$ is not styryl or 4-methoxystyryl.

The invention also includes a pharmaceutical composition comprising a pharmaceutically-acceptable carrier and associated therewith a compound of the formula (II)

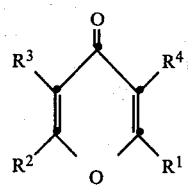

in which $R^1$ is $COOR^5$, $CONHR^5$, cyano, 5-tetrazolyl or $R^6$, where $R^5$ is hydrogen or $C_{1-8}$ alkyl and $R^6$ is phenyl or naphthyl, the phenyl or naphthyl being optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$ and $SR^5$; $R^2$ is $R^6$ or $-CH=CH-R^6$ when $R^1$ is $COOR^5$, $CONHR^5$, cyano or 5-tetrazolyl, or $R^2$ is $-CH=CH-R^6$ when $R^1$ is $R^6$; $R^3$ is hydrogen, $C_{1-6}$ alkyl, halogen, hydroxy or $-OCH_2R^6$, and $R^4$ is hydrogen, $C_{1-6}$ alkyl or halogen; or a pharmaceutically-acceptable salt thereof.

As a further feature of the invention there is included a compound of formula (II) for use as a pharmaceutical, more especially, for use in the treatment of immediate hypersensitivity conditions.

When reference is made to the alkyl group it is intended to include both straight and branched chain alkyls, for example, methyl, ethyl, n-propyl, i-propyl, n-butyl, s-butyl, t-butyl, n-pentyl, n-hexyl, n-heptyl and n-octyl, and an alkyl group preferably includes from 1 to 4 carbon atoms, the most preferred groups being methyl and ethyl.

In the case where $R^1$ is $COOR^5$ and $R^5$ is alkyl, it is to be understood that substituted alkyl groups are also included and are to be regarded as equivalent, in view of the fact that it is often merely necessary to attach an ester group that readily cleaves to give the free acid, and examples of such substituted alkyls include acetoxymethyl, methylthiomethyl, metnhylsulphinylmethyl and methylsulphonylmethyl.

The term, halogen, refers to fluorine, chlorine, bromine or iodine, and is especially chlorine or bromine.

When reference is made to substituted phenyl or naphthyl, there can be one or more substituent on the nucleus, such as 1 to 3 substituents and preferably a single substituent. The substituent $C_{1-4}$ alkoxy is of the form RO where R is an alkyl group which can be any of the examples listed above, and is especially methoxy or ethoxy. The group $N(R^5)_2$ is amino, or mono- or dialkylamino where one or both of the $R^5$ groups is alkyl, for example, methyl or ethyl. A preferred example of the substituent $NHCOR^5$ is the acetamido group in which $R^5$ is methyl. In the case of substituents such as alkylsulphinyl and alkylsulphonyl, the alkyl moiety is preferably methyl or ethyl and $R^5$ in the group $R^5S$ is also preferably methyl or ethyl.

The group $R^6$ is preferably optionally substituted phenyl and when substituted preferably has one or more group selected from halogen, alkyl and alkoxy.

Included in the above general formulae are the salts of compounds, for example, those in which $R^1$ is COOH or 5-tetrazolyl, or compounds in which acidic or basic groups are attached to the substituent $R^6$. The acid addition salts are preferably the pharmaceutically-acceptable, non-toxic addition salts with suitable acids, such as those with inorganic acids, for example hydrochloric, hydrobromic, nitric, sulphuric or phosphoric acids, or with organic acids, such as organic carboxylic acids, for example, glycollic, maleic, hydroxymaleic, fumaric, malic, tartaric, citric, salicylic, o-acetoxybenzoic, nicotinic or isonicotinic acid, or organic sulphonic acids for example methane sulphonic, ethane sulphonic, 2-hydroxyethane sulphonic, toluene-p-sulphonic or naphthalene-2-sulphonic acid. The salts of acid compounds are preferably pharmaceutically-acceptable, non-toxic salts of suitable mineral bases, such as alkali metal hydroxides, especially the potassium or sodium salts, or alkaline earth metal hydroxides especially the calcium salts, or of organic bases such as amines. Apart from the pharmaceutically-acceptable salts, it is to be understood that other salts are included in respect of the novel compounds of the invention, such as for example those with picric or oxalic acid; they may serve as intermediates in the purification of the compounds or in the preparation of other, for example, pharmaceutically-acceptable salts or are useful for the purpose of identification, characterization or purification.

In the above formulae (I) and (II), some of the preferred groups are those which include one or more of the following features (a) $R^1$ is $COOR^5$, $CONHR^5$ or 5-tetrazolyl
(b) $R^1$ is $COOR^5$ and $R^5$ is especially hydrogen or $C_{1-4}$ alkyl
(c) $R^1$ is optionally substituted phenyl
(d) $R^2$ is optionally substituted phenyl
(e) $R^2$ is phenyl optionally substituted with a single substituent selected from halogen, methyl or methoxy.
(f) $R^3$ is hydrogen, halogen or hydroxy, and especially hydrogen
(g) $R^4$ is hydrogen or halogen
(h) $R^4$ is halogen
(i) $R^2$ is —CH=CH—$R^6$ where $R^6$ is optionally substituted phenyl
(j) $R^6$ is optionally substituted phenyl
(k) $R^6$ is phenyl optionally substituted with a single substituent selected from halogen, methyl or methoxy.

Thus preferred groups of compounds are those of the formula

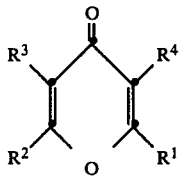

in which (a) $R^1$ is $COOR^5$, $CONHR^5$ or 5-tetrazolyl, $R^2$ is optionally substituted phenyl, $R^3$ is hydrogen and $R^4$ is hydrogen or halogen, or a pharmaceutically-acceptable salt thereof, (b) $R^1$ is $COOR^5$, $CONHR^5$ or 5-tetrazolyl, $R^2$ is —CH=CH—$R^6$ where $R^6$ is optionally substituted phenyl, $R^3$ is hydrogen and $R^4$ is hydrogen or halogen, or a pharmaceutically-acceptable salt thereof, (c) $R^1$ is optionally substituted phenyl, $R^2$ is —CH=CH—$R^6$ is optionally substituted phenyl, $R^3$ is hydrogen and $R^4$ is hydrogen or halogen, or a pharmaceutically-acceptable salt thereof or (d) $R^1$ is $COOR^5$, $R^2$ is optionally substituted phenyl, $R^3$ is hydrogen and $R^4$ is halogen, or a pharmaceutically-acceptable salt thereof.

The present invention includes methods for producing compounds of formula (I) as follows:

(A) Compounds of formula (I) in which $R^1$ is $COOR^5$, $R^2$ is $R^6$, $R^3$ is hydrogen and $R^4$ is hydrogen, alkyl or halogen, can be prepared by reacting a compound of formula (III)

where X is halogen, with a base. The reaction is preferably carried out at a temperature of from 15° C. to 100° C. and the base can be for example, 1,5-diazabicyclo[4.3.0]non-5-ene(DBN) in dimethyl sulphoxide (DMSO), or potassium acetate in ethanol.

The intermediates of formula (III) in which $R^4$ is hydrogen or alkyl, can be prepared by reacting a compound of the formula (IV)

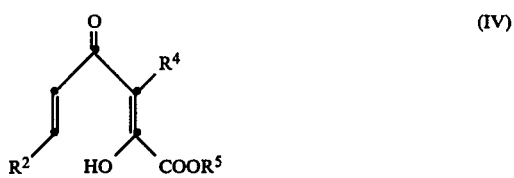

with molecular halogen, for example bromine, preferably in molar equivalent proportions and in a suitable solvent such as for example carbon tetrachloride, chloroform, carbon disulphide or acetic acid. In its turn, the hexanoate (IV) can be prepared by a base catalysed Claisen condensation of a butenone with, for example, diethyl oxalate in ether.

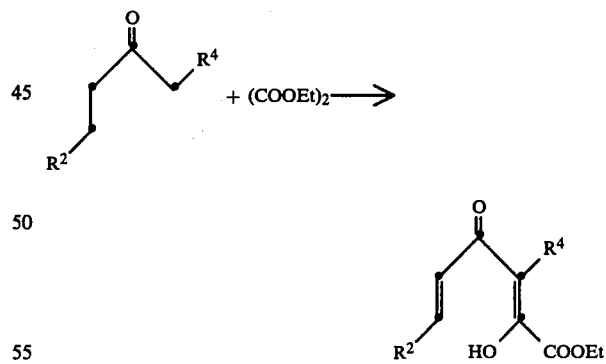

Intermediates of formula (III) in which $R^4$ is halogen can be prepared by reacting a compound of formula (V)

with an excess of molecular halogen, preferably at least two molar equivalents, of for example bromine. In carrying out this reaction it is often found convenient to avoid isolation of the intermediate of formula (III) and to cyclise the compound by direct addition of base to the reaction mixture, as for example:

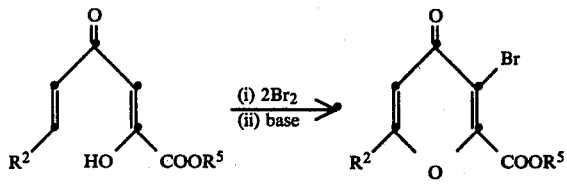

(B) Compounds of formula (I) in which $R^1$ is $COOR^5$, $CONHR^5$, cyano, 5-tetrazolyl or $R^6$, $R^2$ is $R^6$ or —CH=CH—$R^6$, $R^3$ is hydrogen, alkyl or halogen, and $R^4$ is hydrogen, alkyl or halogen, can be prepared by reacting a compound of the formula (VI)

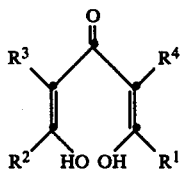

(VI)

with acid. The acid is preferably a mineral acid such as hydrochloric or sulphuric acid and the reaction is most suitably carried out at a temperature of from 0° C. to 100° C. In the case of compounds in which $R^3$ or $R^4$ is halogen, the reaction of halogen, for example bromine, on the corresponding compound in which $R^3$ or $R^4$ is hydrogen, causes the liberation of acid, for example hydrogen bromide, and cyclisation occurs in situ. Alternatively halogenation can be carried out in the presence of base, for example by the combined action of trifluoromethoxysulphonyl chloride and triethylamine, to give a compound of formula V, which in treatment with acid, for example hydrogen chloride, ring closes to give the desired product.

This reaction is particularly suitable for the production of compounds in which $R^1$ is $COOR^5$ and in such instances a choice of suitable conditions will result in hydrolysis and the production of the free acid in which $R^1$ is COOH, or the ester in which $R^1$ is $COOR^5$. For example the former reaction can be made to take place when the 2,4,6-trioxohexanoate (VII) is heated under reflux with aqueous acid, for example hydrochloric acid. The ester group remains attached when non-aqueous conditions, for example concentrated sulphuric acid, at lower temperatures are chosen, as follows

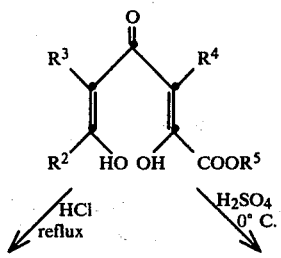

(VII)

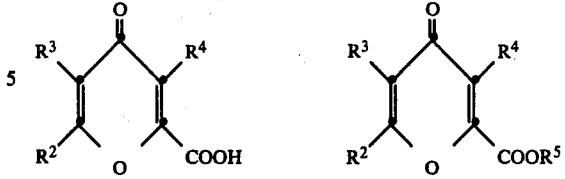

The compounds of formula (VII) in which the groups $R^2$, $R^3$, $R^4$ and $R^5$ have the values defined in formula (I) above, are novel compounds, and form part of the present invention.

The triketone intermediates of formula (VI) are prepared by base catalysed condensation of 1-aryl-1,3-butanediones, which are of a type known in the literature, with an ester of the formula $R^1COOR^5$, as for example $R^2$-CO-CHR$^3$-CO-CH$_2$R$^4$+(COOR$^5$)$_2$→compound (VII) In this reaction an excess amount of base, for example an alkali metal hydride in an inert non-aqueous medium such as dimethoxyethane or DMF, is employed so as to form the di-anion of the butanedione.

The 1-aryl-1,3-butanediones are known compounds examples of which are described in J.Am.Chem.Soc.56, 2665 (1934) and J.Am.Chem.Soc.70, 4023 (1948). In the former reference the compounds are prepared by acylation of the appropriate acetophenone with a combination of ester and base, and in the latter reference by acylation of the appropriate acetophenone with anhydrides and boron trifluoride.

(C) Compounds of formula (I) in which $R^1$, is $COOR^5$ or $R^6$, $R^2$ is —CH=CH—$R^6$, $R^3$ is hydrogen, alkyl, halogen, hydroxy or —OCH$_2$R$^6$, and $R^4$ is hydrogen, alkyl or halogen can be prepared by reacting an aldehyde of formula $R^6$CHO with a pyranone of formula

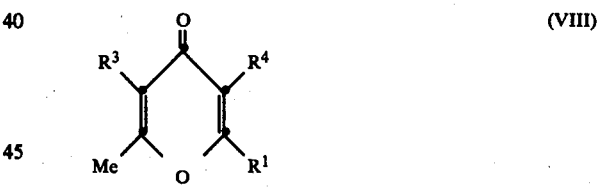

(VIII)

This condensation reaction is preferably carried out in the presence of a base such as for example sodium ethoxide in ethanol, at a temperature of from 0° C. to 100° C., for instance as follows

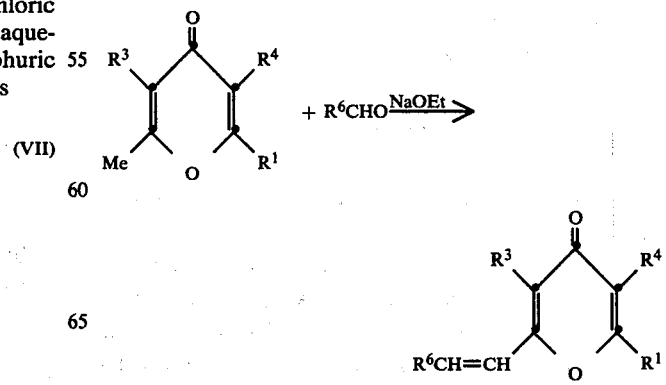

When $R^1$ is $COOR^5$ and $R^5$ is alkyl, simultaneous hydrolysis of the ester may occur to give the free acid in which $R^1$ is COOH.

The intermediate (VIII) in which $R^1$ is $R^6$, can be prepared by cyclisation of a triketone with acid according to methods in the literature, see for example, J.Am.-Chem.Soc.80, 6360 (1958), as follows

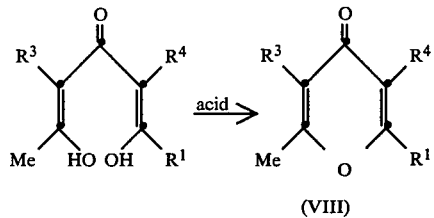

(VIII)

When the intermediate (VIII) is a compound in which $R^1$ is other than $R^6$, it can be prepared, for example, by mild acidic cyclisation of the Claisen condensation product of an acetylacetone monoketal and dialkyl oxalate.

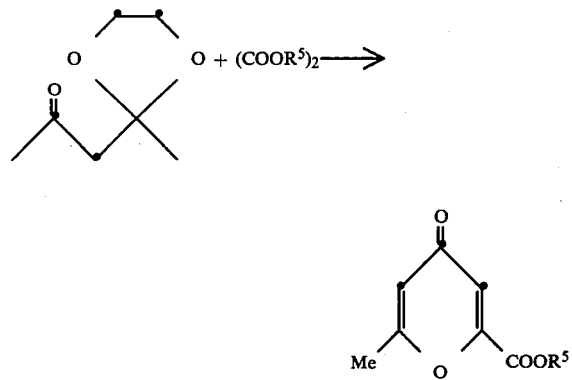

(D) Compounds of formula (I) in which $R^1$ is $COOR^5$, $R^2$ is $R^6$, $R^3$ is halogen or hydroxy and $R^4$ is hydrogen, alkyl or halogen, can be prepared by reacting a compound of formula.

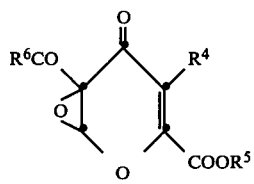

(IX)

with acid. The reaction is preferably carried out at a temperature of from 0° C. to 110° C. Treatment with a non-nucleophilic acid, for example formic or perchloric acid, yields compounds of formula (I) in which $R^3$ is hydroxy. Treatment with hydrogen halide yields the ester in which $R^3$ is halogen under mild conditions and under more vigorous conditions the acid, for example

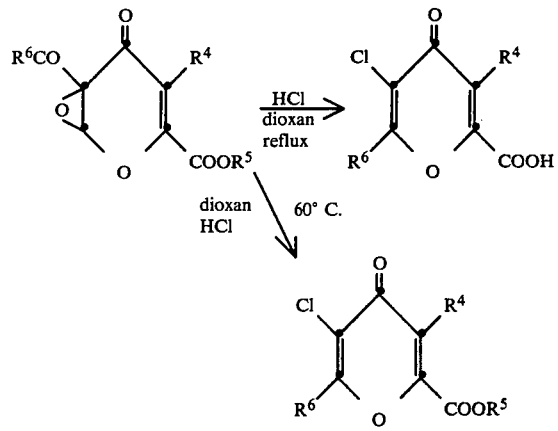

The starting material (IX) can be prepared by the action of an oxidising agent, for example hydrogen peroxide, on the corresponding 5-benzoyl pyranone

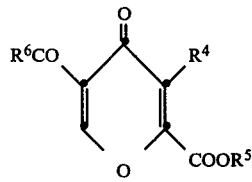

Such compounds can be prepared by reacting a compound of formula

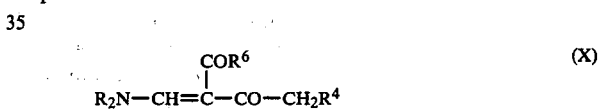

(X)

where R is $C_{1-6}$ alkyl, with a dialkyl oxalate $(COOR^5)_2$, in the presence of a base, followed by acidification. The reaction of dialkyl oxalate with the compound of formula (X) preferably takes place in an organic solvent such as an alcoholic or ethereal solvent, requiring the presence of a base such as an alkali metal alkoxide or hydride. Treatment of the product with acid such as a mineral acid, for example hydrochloric acid, gives the desired compound. The intermediate (X) can be prepared by reacting a ketone of formula

with a dialkylamide dialkylacetal of formula

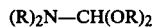

or by reacting a compound of formula

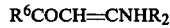

with an acylating agent having the formula $R^4CH_2COX$, where X is halogen, or $(R^4CH_2CO)_2O$.

(E) Compounds of formula (I) in which $R^1$ is COOH, $R^2$ is $R^6$, $R^3$ is hydroxy or $-OCH_2R_6$ and $R^4$ is hydrogen, alkyl or halogen, can be made by oxidising a compound of formula (XI)

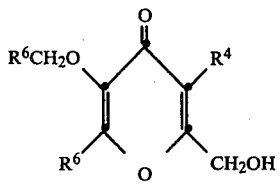

followed when $R^3$ is hydroxy by cleavage of the $R^6CH_2$ group. In this process, the oxidising agent can be, for example chromic oxide, and the reaction is preferably carried out at a temperature of from 0° C. to 40° C. When cleavage of the benzyl ether is required, well-known reagents can be used such as an acid mixture, for example hydrogen bromide/acetic acid

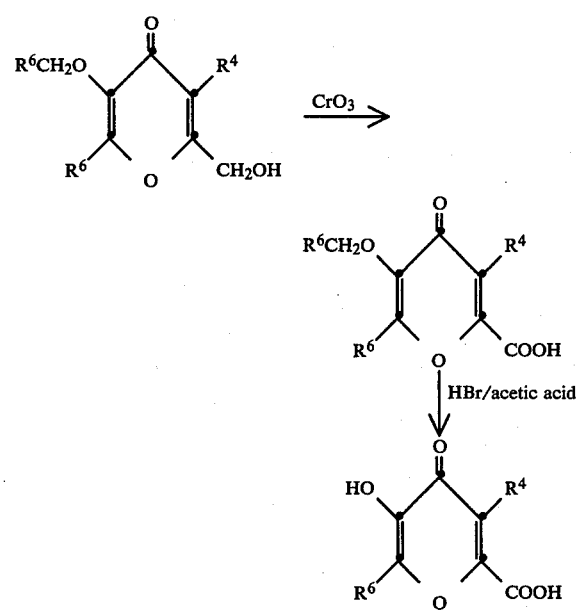

Compounds of formula (XI) can be prepared by arylation of a compound of formula

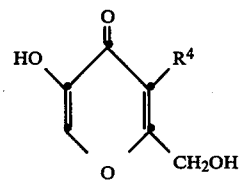

with a compound of formula $(R_6)_2$ IX where X is halogen, for example bromine, in the presence of base for example sodium methoxide in methanol, at a reaction temperature of 20° C. to 80° C. Conversion of the hydroxy group to $R^6CH_2O-$ is accomplished by a standard aralkylation technique.

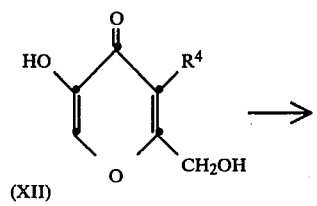

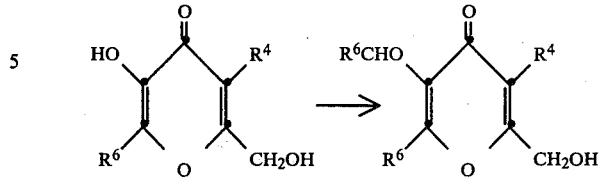

Compounds of formula (XII) are known and, for example, the compound in which $R^4$ is hydrogen is widely available as kojic acid.

(F) Compounds of formula (I) in which $R^1$ is $COOR^5$, $R^2$ is $R^6$, $R^3$ is hydrogen and $R^4$ is hydrogen, alkyl or halogen, can be prepared by reacting a compound of formula (XIII)

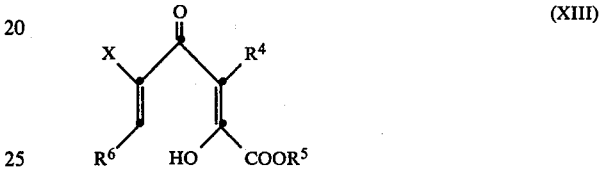

where X is halogen, with a base. In this reaction the compound of formula (XIII) is cyclised by for example a base such as DBN in DMSO, preferably at a temperature of from 15° C. to 50° C. Compounds of formula (XIII) can be prepared by the condensation of a vinyl halide with dialkyl oxalate, as follows

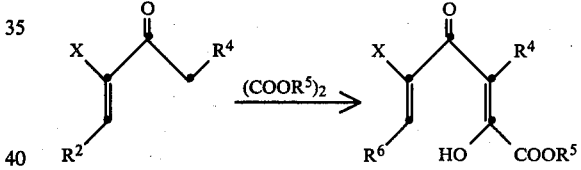

It will be appreciated that compounds prepared by the above processes in which $R^1$ is COOH or $COOR^5$ can readily be converted into compounds with other $R^1$ substituents, as follows.

Compounds in which $R^1$ is $COOR^5$ where $R^5$ is $C_{1-8}$ alkyl, can be converted to the corresponding free acid in which $R^1$ is COOH by hydrolysis in the presence of acid such as a mineral acid, for example hydrochloric acid, or by reaction with boron trihalide in an inert solvent, with lithium iodide in DMF, or with sodium iodide in a mixture of methyl ethyl ketone and pyridine. Such methods are well known in the art. Conversely, compounds in which $R^1$ is $COOR^5$ where $R^5$ is $C_{1-8}$ alkyl can be prepared from the free acid by esterification of the free carboxyl group with the appropriate alcohol or by treatment with alkyl halide in the presence of base. Salts of the free acid can, of course, be prepared simply by reaction with alkali.

Compounds in which $R^1$ is $CONHR^5$ can be prepared by reacting a compound in which $R^1$ is $COOR^5$ where $R^5$ is $C_{1-8}$ alkyl, with ammonia or the appropriate amine of formula $R^5NH_2$, or they can be prepared by the reaction of ammonia or an amine of formula $R^5NH_2$ with the appropriate acyl chloride which can in its turn be derived from the free carboxyl derivative by the reaction of thionyl chloride. Such reactions are well known in the art.

Compounds in which $R^1$ is CN can be prepared by dehydration of the amides in which $R^1$ is $CONH_2$, a convenient dehydrating agent being, for example, a mixture of triphenylphosphine and carbon tetrachloride.

Compounds in which $R^1$ is 5-tetrazolyl can be prepared by reaction of the cyano derivative prepared as above with, for example sodium azide and ammonium chloride in dimethylformamide. Salts can be prepared from the 5-tetrazolyl derivatives by the addition of base according to standard techniques.

It will also be appreciated that many of the compounds of formula (I) can be converted one to another by introduction of groups into the $R^6$ nucleus employing simple and well known chemical reactions. When a nitro substituent is desired in the $R^6$ group, the unsubstituted compound can be nitrated with a mixture of concentrated nitric and sulphuric acids by the conventional method. The nitro compound can subsequently be converted to other substituents such as amine or acylamino. The amino compound may be diazotised and the resultant diazonium salt converted to a variety of other products, for example, by decomposition in an alcohol to yield the corresponding alkoxy substituted compound or by reaction with a cuprous halide to yield the corresponding halo substituted compound of formula (I). Hydroxy substituted compounds can be prepared from the corresponding methoxy compounds by cleavage with, for example, boron tribromide. Alkyl sulphonyl and alkyl sulphinyl substituted aryl derivatives can be prepared by oxidation of the corresponding alkylthio compound by reaction for example with m-chloroperoxybenzoic acid.

When $R^3$ in formula (I) is $R^6CH_2O$, it will be appreciated that such compounds can readily be prepared from the corresponding hydroxy derivatives by standard alkylation techniques.

Although compounds of formulae III, IV, V, VI, VII and XIII, for example, have been shown in their enol form, they also exist as keto compounds and in most systems as a tautomeric mixture.

The pyranones of formulae (I) and (II) and their pharmaceutically-acceptable salts, have been shown to be useful in the prophylactic and therapeutic treatment of immediate hypersensitivity diseases including asthma and in the alleviation of status asthmaticus. They are also of low toxicity.

This activity has been demonstrated in guinea pigs using either the "guinea-pig chopped lung test" described by Mongar and Schild in the Journal of Physiology (London) 131, 207(1956) or Brocklehurst in the Journal of Physiology (London) 151, 416 (1960), or the "Herxheimer" test described in the Journal of Physiology (London) 117, 251(1952). For example have exhibited a greater than 15 percent inhibition of mediator release in the "guinea-pig chopped lung test". In the "Herxheimer" test, which is based on an allergic bronchospasm induced in guinea pigs closely resembling an asthmatic attack in man, compounds have exhibited activity at dosages ranging from 25 mg/kg to 200 mg/kg.

The compounds may be administered by various routes, although it is a special feature of the compounds that they are effective when administered orally. Thus the compounds may be administered by the oral and rectal routes, topically and pareneterally e.g. by injection, being usually employed in the form of a pharmaceutical composition. Such compositions are prepared in a manner well known in the pharmceutical art and normally comprise at least one active compound or salt of the invention in association with a pharmaceutically-acceptable carrier therefor. In making the composition of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus the composition can be in the form of tablets, lozenges, sachets, cachets, elixirs, suspensions, aerosols (as a solid or in a liquid medium), ointments containing for example up to 10% by weight of the active compound, soft and hard gelatin capsules, suppositories, injection suspensions and sterile packaged powders.

Some examples of suitable carriers are lactose, dextrose, sucrose, sorbitol, mannitol, starches, gum acacia, calcium phosphate, alignates, tragacanth, gelatin, syrup, methyl cellulose, methyl- and propyl- hydroxybenzoate, talc, magnesium stearate or mineral oil. The compositions of the invention may, as is well known in the art, be formulated so as to provide quick, sustained or delayed release of the active ingredient after administration to the patient.

Preferably the compositions are formulated in a unit dosage form, each dosage containing from 5 to 500 mg, more usually 25 to 200 mg, of the active ingredient. The term "unit dosage form" refers to physically discrete units suitable as unitary dosages for human objects and animals, each unit containing a predetermined quantity of active material calculated to produce the desired therapeutic effect, in association with the required pharmaceutical carrier.

The active compounds are effective over a wide dosage range and for example dosages per day will normally fall within the range of 0.5 to 300 mg/kg. and in the treatment of adult humans, more usually in the range of from 5 to 100 mg/kg. However it will be understood that the amount of the compound actually administered will be determined by a physician, in the light of the relevant circumstances including the condition to be treated, the choice of compound to be administered and the chosen route of administration and therefore the above dosage ranges are not intended to limit the scope of the invention in any way.

The following Examples illustrate the invention.

EXAMPLE 1

Ethyl 6-(4-chlorophenyl)-2,4-dioxo-hex-5-enoate.

A solution of 4-(4-chlorophenyl)-3-buten-2-one (27.1 g) and diethyl oxalate (21.9 g) in dry diethyl ether (200 ml) was added dropwise over 15 minutes to a stirred suspension of sodium ethoxide (3.45 g of sodium dissolved in absolute ethanol and excess ethanol evaporated off) in dry diethyl ether (400 ml) cooled to 5°–10° C. by an ice bath. A yellow solid began to precipitate after 5 minutes.

After 2 hours at room temperature the solid (sodium salt of product) was filtered off and washed with ether (200 ml). The solid was then stirred vigorously for 30 minutes with dilute hydrochloric acid (1 M, 600 ml) and the product filtered and washed with water. Recrystallisation from ethanol yielded the title product as yellow needles (mp 117°–118° C.).

EXAMPLES 2–4

The following compounds were prepared by the method of Example 1

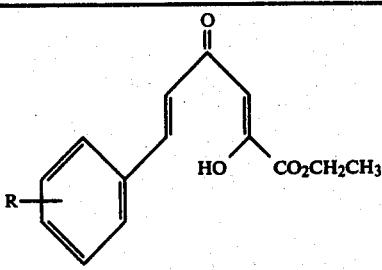

| Example | R | mp °C. | Solvent of recrystallisation |
|---|---|---|---|
| 2 | 2-Cl | 69–70 | ethanol |
| 3 | 4-CH₃ | 117–118 | ethanol |
| 4 | 4-SCH₃ | 99–102 | ethanol |

EXAMPLE 5

Ethyl 5,6-dibromo-2,4-dioxo-6-(4-methoxyphenyl)-hexanoate.

Bromine (8.7 g) in glacial acetic acid (15 ml) was added dropwise over 1 hour to a stirred suspension of ethyl 2,4-dioxo-6-(4-methoxyphenyl)-hex-5-enoate (15.0 g) in acetic acid (54 ml) cooled to 15°–20° C. The mixture turned red and the reactant dissolved to give a clear solution. After 30 minutes the product began to precipitate as a yellow solid.

After 1 hour at room temperature, water (100 ml) and petroleum ether 40°–60° C. (50 ml) were added and the solid was filtered off, washed with water, and dried under vacuum. Petroleum ether 80°–100° C. was employed as solvent of recrystallisation. The hot solution was decanted from a small quantity of insoluble sticky material and gave the title product as yellow powdery crystals (mp 111° C.).

EXAMPLE 6

Ethyl 5,6-dibromo-2,4-dioxo-6-(4-methylthiophenyl)-hexanoate

The above compound was prepared by the method of Example 5 and recrystallised from petroleum ether 80°–100° C. (mp 123°–125° C.).

EXAMPLE 7

Ethyl 5,6-dibromo-2,4-dioxo-6-(2-methoxyphenyl)-hexanoate

The above compound was prepared by bromination as in Example 5 using a mixture of carbon disulphide and chloroform as reaction solvent. The solvent component of the reaction mixture was evaporated off and the residue was recrystallised from ethanol-petroleum ether 60°–80° C. to give the above product (mp 113°–115° C.).

EXAMPLE 8

Ethyl 6-(4-methoxyphenyl)-4-oxo-4H-pyran-2-carboxylate 1,5-Diazabicyclo[4.3.0]non-5-ene (3.2 g) was added dropwise to a stirred solution of ethyl 5,6-dibromo-2,4-dioxo-6-(4-methoxyphenyl)hexanoate (5.6 g) in dimethylsulphoxide (30 ml) maintained at a temperature of 15°–20° C. After 30 minutes at room temperature, water (50 ml) and petroleum ether 40°–60° C. (20 ml) were added with cooling. The yellow solid which precipitated was filtered off and recrystallised from ethanol-water. A second recrystallisation from ethyl acetate-petroleum ether 60°–80° C. yielded the title product as yellow needles (mp 131°–133° C. with sublimation).

EXAMPLE 9

Ethyl 6-(4-methylthiophenyl)-4-oxo-4H-pyran-2-carboxylate

The above compound was prepared by the method of Example 8 and recrystallised from petroleum ether 80°–100° C. (mp 119°–123° C.).

EXAMPLE 10

Ethyl 6-(2-methoxyphenyl)-4-oxo-4H-pyran-2-carboxylate

A solution of ethyl 5,6-dibromo-2,4-dioxo-6-(2-methoxyphenyl)hexanoate (9.5 g) and potassium acetate (10.0 g) in absolute ethanol (100 ml) was heated under reflux for 5 hours and then allowed to stand at room temperature overnight. The mixture was evaporated and the resulting brown residue dissolved in water (150 ml) and diethyl ether (150 ml). The ethereal solution was washed with water and saturated aqueous sodium chloride, dried over anhydrous magnesium sulphate, filtered and evaporated to give a tan coloured solid. Recrystallisation from ethanol-water yielded the title product as pale yellow needles (mp 78°–81° C.).

EXAMPLE 11

Ethyl 6-(2-chlorophenyl)-4-oxo-4H-pyran-2-carboxylate

Bromine (11.4 g) in chloroform (70 ml) was added dropwise over 30 minutes to a stirred solution of ethyl 6-(2-chlorophenyl)-2,4-dioxohex-5-enoate (20.0 g) in chloroform (200 ml) cooled to 5°–10° C. The bromine colour rapidly faded. After an hour at room temperature the solution was evaporated and the crude ethyl 6-(2-chlorophenyl)-5,6-dibromo-2,4-dioxo-hexanoate dissolved in dimethylsulphoxide (200 ml).

1,5-Diazabicyclo[4.3.0]non-5-ene (17.4 g) was added to the stirred solution maintained at 15°–20° C. After an hour at room temperature, water (300 ml) was added to the cooled mixture and the resulting brown precipitate was filtered off. Recrystallisation from ethanol-water and then recrystallisation twice from petroleum ether 80°–100° C., gave the title product as yellow needles (mp 104°–106° C.).

EXAMPLE 12

Ethyl 6-(4-chlorophenyl-4-oxo-4H-pyran-2-carboxylate

The above compound was prepared by the method of Example 11 and recrystallised from ethanol-water (mp 131°–135° C.).

EXAMPLE 13

6-(4-Methylphenyl)-4-oxo-4H-pyran-2-carboxylic acid

Ethyl 6-(4-methylphenyl)-4-oxo-4H-pyran-2-carboxylic was prepared from ethyl 2,4-dioxo-6-(4-methylphenyl)-hex-5-enoate by the method of Example 11 and recrystallised from ethanol-water (mp 140°–146° C.). This ester was hydrolysed with concentrated hydrochloric acid under reflux, to give the title product (mp 237°–238° C.).

EXAMPLE 14

Ethyl 3-bromo-6-(4-chlorophenyl)-4-oxo-4H-pyran-2-carboxylate

A solution of bromine (7.06 ml) in chloroform (70 ml) was added dropwise to a stirred solution of ethyl 6-(4-chlorophenyl)-2,4-dioxohex-5-enoate (19.2 g) in chloroform (300 ml) at 5° to 10° C. The solution was stirred for 30 minutes at room temperature then evaporated to a yellow oil. This crude tribromide was dissolved in dimethylsulphoxide (150 ml), and 1,5-diazabicyclo[4.3.0]-non-5-ene (16.9 g) was added at 20° to 25° C. The mixture was stirred for 30 minutes at room temperature then diluted with ice-water (300 ml) to precipitate a sticky brown solid. A solution of this crude product in chloroform was passed down a short column of silica-gel (100 g) and then evaporated. The residual solid was washed with ethyl acetate-petroleum ether 60°–80° C., then recrystallised from ethyl acetate-petroleum ether 60°–80° C. to give the title product as yellow needles (mp 146°–149° C.).

EXAMPLE 15

Ethyl 3-bromo-6-(2-chlorophenyl)-4-oxo-4H-pyran-2-carboxylate

This compound was prepared by the method described in Example 14 (mp 104°–107° C.).

EXAMPLE 16

3-Bromo-4-oxo-6-phenyl-4H-pyran-2-carboxylic acid

Ethyl 3-bromo-4-oxo-6-phenyl-4H-pyran-2-carboxylate was prepared by the method given in Example 14 (mp 135°–138° C.). This ethyl ester was hydrolysed as described below in Example 33 to give the title product (mp 247° C. with decomposition).

EXAMPLE 17

Ethyl 6-(4-hydroxyphenyl)-4-oxo-4H-pyran-2-carboxylate

Boron tribromide (5.0 g) was added dropwise to a stirred solution of ethyl 6-(4-methoxyphenyl)-4-oxo-4H-pyran-2-carboxylate (5.48 g) in dichloromethane (40 ml) cooled to 0°–5° C. After 2 hours at below 5° C., water was cautiously added to the reaction mixture, with cooling, and the yellow solid which precipitated was filtered off. Recrystallisation from ethanol and then from ethyl acetate gave the title product as yellow crystals (mp 213°–215° C.).

EXAMPLES 18 & 19

Ethyl 6-(3-nitrophenyl)-4-oxo-4H-pyran-2-carboxylate and Ethyl 6-(2-nitrophenyl)-4-oxo-4H-pyran-2-carboxylate A solution of concentrated sulphuric acid (20 ml) and concentrated nitric acid (70%, 20 ml) was added dropwise to a stirred solution of ethyl 6-phenyl-4-oxo-4H-pyran-2-carboxylate (48.8 g) in concentrated sulphuric acid (200 ml) cooled to −10° to −15° C. After 30 minutes the clear solution was poured on to iced water (100 ml) and petroleum ether 40°–60° (200 ml) with stirring. The white solid which precipitated was filtered off and washed with water. The crude product contained a mixture of the 2-, 3-, and 4-nitrophenyl isomers.

Recrystallisation from ethanol followed by a second recrystallisation from toluene gave ethyl 6-(3-nitrophenyl)-4-oxo-4H-pyran-2-carboxylate as a white solid (mp 148°–152° C.).

Ethyl 6-(2-nitrophenyl)-4-oxo-4H-pyran-2-carboxylate was obtained by evaporation of mother liquors from the preceding ethanol recrystallisation, followed by recrystallisation from diethyl ether and a second recrystallisation from toluene (mp 140°–142° C.).

EXAMPLE 20

6-(4-Nitrophenyl)-4-oxo-4H-pyran-2-carboxylic acid

Ethyl 6-(4-nitrophenyl)-4-oxo-4H-pyran-2-carboxylate was obtained by evaporation of the mother liquors of the first toluene recrystallisation in Example 18 followed by separation using column chromatography and recrystallisation from ethyl acetate-petroleum ether 60°–80° C., (mp 160°–162° C.). The ester was hydrolysed by concentrated hydrochloric acid heated under reflux, to give the title product (mp 248°–250° C. with decomposition).

EXAMPLE 21

Ethyl 6-(3-aminophenyl)-4-oxo-4H-pyran-2-carboxylate

The above compound was prepared by the method described below in Example 59 stirring with the product of Example 18, and recrystallised from ethanol-water (mp 178°–181° C.).

EXAMPLE 22

Ethyl 6-(3-acetamidophenyl)-4-oxo-4H-pyran-2-carboxylate

This compound was prepared by the method described below in Example 59 from the product of Example 21, and was recrystallised from ethanol-water (mp 205°–207° C.).

EXAMPLE 23

6-(2-Chlorophenyl)-4-oxo-4H-pyran-2-carboxylic acid

A mixture of ethyl 6-(4-chlorophenyl)-4-oxo-4H-pyran-2-carboxylate (3.9 g) and concentrated hydrochloric acid (40 ml) was heated under reflux for 2 hours. The reactant dissolved on warming and a solid began to precipitate. Water (40 ml) was added to the cooled mixture and the resulting buff solid yielded the title product as off-white needles (mp 241°–246° C. with decomposition).

EXAMPLES 24–31

The following compounds were prepared by the method of Example 23.

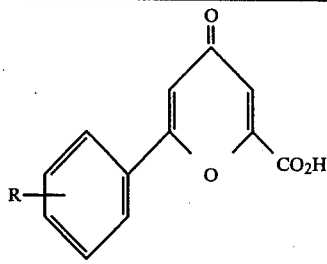

| Example | R | mp °C. | Solvent of recrystallisation |
| --- | --- | --- | --- |
| 24 | 4-Cl | 264–265 | water |
| 25 | 2-OCH$_3$ | 257–260 | water |
| 26 | 4-OCH$_3$ | 250–253 | acetic acid |
| 27 | 4-OH | 261–265 | acetic acid |
| 28 | 4-SCH$_3$ | 230–236 | acetic acid - water |
| 29 | 3-NO$_2$ | 290–291 | acetic acid - water |
| 30 | 2-NO$_2$ | 257–258 | acetic acid - water |
| 31 | 3-NH$_2$ | >300 | water |

EXAMPLE 32

6-(2-Hydroxyphenyl)-4-oxo-4H-pyran-2-carboxylic acid

Ethyl 6-(2-hydroxyphenyl)-4-oxo-4H-pyran-2-carboxylate was prepared by the method of Example 17 (mp 213°–215° C.). This ethyl ester was hydrolysed as in Example 23 to give the title product (mp 256°–258° C.).

EXAMPLE 33

3-Bromo-6-(2-chlorophenyl)-4-oxo-4H-pyran-2-carboxylic acid

A stirred solution of ethyl 3-bromo-6-(2-chlorophenyl)-4-oxo-4H-pyran-2-carboxylate (2.3 g) and boron tribromide (2.5 ml) in dichloromethane (25 ml) was heated under reflux for 4 hours. A tan solid precipitated out. Water (25 ml) was added to the cooled mixture and the yellow solid was filtered off. Recrystallisation from glacial acetic acid yielded the title product as off-white needles (mp 205°–207° C. with decomposition).

EXAMPLE 34

3-Bromo-6-(4-chlorophenyl)-4-oxo-4H-pyran-2-carboxylic acid

The above compound was prepared by the method of Example 33 (mp 203°–205° C. with decomposition).

EXAMPLE 35

6-(3-Octanamidophenyl)-4-oxo-4H-pyran-2-carboxylic acid

Ethyl 6-(3-octanamidophenyl)-4-oxo-4H-pyran-2-carboxylate was prepared by the method described below in Example 59 using octanoic anhydride as the acylating agent and was recrystallised from ethanol-water (mp 176° C.). This ethyl ester was hydrolysed by the method of Example 23 to give the title product (mp 242°–247° C. with decomposition).

EXAMPLE 36

4-Oxo-6-phenyl-5-phenylmethoxy-4H-pyran-2-carboxylic acid

A stirred solution of 5-hydroxy-2-hydroxymethyl-4H-pyran-4-one (10.2 g), diphenyliodonium bromide (26.0 g) and sodium methoxide (4.3 g) in methanol (100 ml) was heated at 50° C. for 20 hours. The solution was cooled and treated with water (200 ml) and petroleum ether 60°–80° C. (100 ml) and the solid product was recrystallised from ethanol-water and then from ethyl acetate-petroleum ether 60°–80° C. to give 3-hydroxy-6-hydroxymethyl-2-phenyl-4H-pyran-4-one (mp 151°–154° C.).

A mixture of this 3-hydroxy compound (4.1 g), anhydrous potassium carbonate and benzyl bromide (3.42 g) in dry dimethylformamide (40 ml) was heated at 60° C. for an hour. Water (100 ml) was added to the cooled mixture and the resulting yellow precipitate of 6-hydroxymethyl-2-phenyl-3-phenylmethoxy-4H-pyran-4-one filtered and recrystallised from ethanol-water (mp 108°–110° C.).

Jones reagent (7.30 ml, 2.67 M) was added dropwise to a stirred solution of this hydroxymethyl compound (4.5 g) in acetone (300 ml) cooled to 5°–10° C. After standing overnight at room temperature the mixture was filtered and the filtrate was evaporated to a pale green solid. This solid was dissolved in aqueous sodium bicarbonate and the pricipitate which separated out on acidification was filtered off. Recrystallisation from acetic acid-water gave the title product as off-white crystals (mp 161°–170° C.).

EXAMPLE 37

6-(4-Methoxyphenyl)-4-oxo-4H-pyran-2-carboxamide

A mixture of ethyl 6-(4-methoxyphenyl)-4-oxo-4H-pyran-2-carboxylate (27.4 g), ammonia solution (30%, 50 ml) and ethanol (300 ml) was heated under reflux for an hour. The yellow solid which precipitated on cooling was filtered off and recrystallised from acetic acid-ethanol to yield the title product (mp 303°–308° C. with decomposition).

EXAMPLES 38 & 39

The following compounds were prepared by the method of Example 37

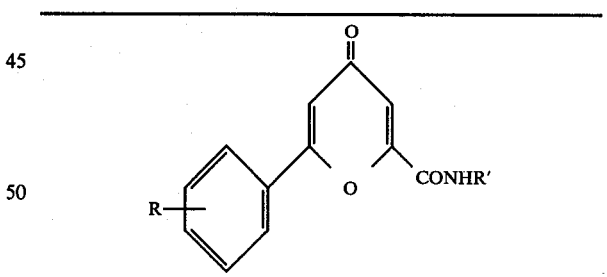

| Example | R | R' | mp °C. | Solvent of recrystallisation |
| --- | --- | --- | --- | --- |
| 38 | 4-OCH$_3$ | CH$_3$ | 262–264 | ethanol-water |
| 39 | 4-OCH$_3$ | n-C$_4$H$_9$ | 107–108 | ethyl acetate-petroleum ether 60–80° C. |

EXAMPLE 40

4-Oxo-6-phenyl-4H-pyran-2-carbonitrile

A mixture of 4-oxo-6-phenyl-4H-pyran-2-carboxamide (4.26 g), triphenylphosphine (10.48 g) and triethylamine (2.8 ml) in carbon tetrachloride (40 ml) and dichloromethane (80 ml) was stirred at room temperature for 4 hours. The reactant slowly dissolved. Dilute hydrochloric acid (1 M, 50 ml) and chloroform (100 ml) were added. The organic layer was separated, washed with water, dried over anhydrous magnesium sulphate, filtered and evaporated. The brown residue was recrystallised twice from carbon tetrachloride to yield the title product as off-white crystals (mp 146°-149° C.).

EXAMPLE 41

6-(4-Methoxyphenyl)-4-oxo-4H-pyran-2-carbonitrile

The above compound was prepared by the same method as Example 40 and was recrystallised from ethanol (mp 148°-150° C.).

EXAMPLE 42

6-Phenyl-2-tetrazol-5-yl-4H-pyran-4-one

A mixture of 4-oxo-6-phenyl-4H-pyran-2-carbonitrile (1.10 g), sodium azide (0.45 g) and ammonium chloride (0.37 g) in dry dimethylformamide (10 ml) was stirred at room temperature for 2 hours. A precipitate formed. Dilute hydrochloric acid (1 M, 20 ml) was added and the resulting white solid was filtered off. Recrystallisation from acetic acid yielded the title product as white crystals (251°-254° C. with decomposition).

EXAMPLE 43

6-(4-Methoxyphenyl)-2-tetrazol-5-yl-4H-pyran-4-one

The above compound was prepared by the method of Example 42 and was recrystallised from acetic acid-water (mp 237°-240° C. with decomposition).

EXAMPLE 44

Ethyl 5-chloro-4-oxo-6-phenyl-4H-pyran-2-carboxylate

A stirred solution of benzoylacetone (16.2 g) and dimethylformamide dimethylacetal (16.2 ml) was heated on an oil bath at 80° C. for 40 minutes. Volatile materials were removed under vacuum and the residue was crystallised from ether to give 2-(dimethylaminomethylene)-1-phenyl-1,3-butanedione (mp 81°-83° C.).

A solution of this enamine (19.0 g) and diethyl oxalate (23.7 ml) in ethanol (120 ml) was added to a solution of sodium ethoxide prepared by dissolving sodium (3.0 g) in ethanol (60 ml). The solution was stirred for 6 hours at room temperature then acidified with 5 M hydrochloric acid solution (100 ml). The mixture was allowed to stand overnight and was then cooled and diluted with water (300 ml) to give pale crystals of ethyl 5-benzoyl-4-oxo-4H-pyran-2-carboxylate (mp 84°-86° C.).

Solid sodium acetate (2.0 g) was added to a stirred solution of this ester (5.4 g) in dimethylformamide (80 ml) at 0°-5° C. 30% Hydrogen peroxide solution (10 ml) was added dropwise over 15 minutes and the mixture was stirred for a further 1 hour at 0°-5° C. then slowly diluted with water (240 ml). The solid product was dried and recrystallised from ether-petroleum ether 40°-60° C. to give the epoxide, ethyl 6-benzoyl-5-oxo-2,7-dioxabicyclo-[4.1.0]hept-3-ene-3-carboxylate (mp 96°-98° C.).

A solution of this epoxide (1.9 g) in dioxan (30 ml) and 5 M hydrochloric acid (10 ml) was heated at 55°-60° C. for 1½ hours, cooled, diluted with water and extracted with ethyl acetate. The extract was washed with sodium bicarbonate solution, dried and evaporated, and the solid residue was recrystallised from ether-petroleum ether 40°-60° C. to give the title product (mp 103°-105° C.).

EXAMPLE 45

Ethyl 5-hydroxy-4-oxo-6-phenyl-4H-pyran-2-carboxylate

A solution of ethyl 6-benzoyl-5-oxo-2,7-dioxabicyclo[4.1.0]hept-3-ene-3-carboxylate (3.5 g) in 98-100% formic acid (50 ml) was heated under reflux for 1½ hours, cooled, diluted with water and extracted with ethyl acetate. The extract was washed with excess sodium bicarbonate solution, dried and evaporated and the solid residue was crystallised twice from chloroform-petroleum ether 60°-80° C. to give the title product (mp 155°-157° C.).

EXAMPLE 46

Ethyl 6-(4-chlorophenyl)-5-hydroxy-4-oxo-4H-pyran-2-carboxylate

The epoxide, ethyl 6-(4-chlorobenzoyl)-5-oxo-2,7-dioxabicyclo[4.1.0]hept-3-ene-3-carboxylate (mp 100° C.) was prepared by a method similar to that described in Example 44 and reacted with formic acid as described in Example 45 to give the title product (mp 157°-159° C.).

EXAMPLE 47

Ethyl 5-hydroxy-6-(4-hydroxyphenyl)-4-oxo-4H-pyran-2-carboxylate

The epoxide, ethyl 6-(4-methoxybenzoyl)-5-oxo-2,7-dioxabicyclo[4.1.0]hept-3-ene-3-carboxylate (mp 96° C.) was prepared by a method similar to that described in Example 44 and reacted with formic acid as described in Example 45 to give ethyl 5-hydroxy-6-(4-methoxyphenyl)-4-oxo-4H-pyran-2-carboxylate (mp 163°-164° C.).

Boron tribromide (1.2 ml) was added dropwise to a stirred solution of this ester (1.2 g) in methylene chloride (50 ml) with cooling. The mixture was stirred for 6 hours at room temperature then carefully diluted with water (25 ml). The solid which formed was recrystallised from ethanol to give the title product (mp 228°-232° C.).

EXAMPLE 48

5-Hydroxy-6-(4-methoxyphenyl)-4-oxo-4H-pyran-2-carboxylic acid

A solution of ethyl 5-hydroxy-6-(4-methoxyphenyl)-4-oxo-4H-pyran-2-carboxylate (2.6 g), prepared as described in Example 47, in dioxan (30 ml) and concentrated hydrochloric acid (20 ml) was heated on a steam bath for 2 hours. The solid product was recrystallised from ethanol to give the title product (mp 258°-260° C. with decomposition).

EXAMPLE 49

5-Chloro-4-oxo-6-phenyl-4H-pyran-2-carboxylic acid

A solution of ethyl 6-benzoyl-5-oxo-2,7-dioxabicyclo[4.1.0]-hept-3-ene-3-carboxylate (2.9 g) prepared as in Example 44, in dioxan (30 ml) and concentrated hydrochloric acid (10 mol) was heated under reflux for 2 hours. The solution was evaporated under vacuum and the solid residue was crystallised from ethyl acetate-petroleum ether 60°-80° C. and then from dioxan-water to give the title product (mp 216°–218° C. with decomposition).

EXAMPLE 50

6-(4-Chlorophenyl)-5-hydroxy-4-oxo-4H-pyran-2-carboxylic acid

The above compound was prepared by the method described in Example 48 (mp 255°–256° C. with decomposition).

EXAMPLE 51

2-[2-(4-Chlorophenyl)ethenyl]-6-phenyl-4H-pyran-4-one

2-Methyl-6-phenyl-4H-pyran-4-one (3.7 g) was dissolved in sodium ethoxide solution prepared by dissolving sodium (0.46 g) in ethanol (50 ml). A solution of 4-chlorobenzaldehyde (5.6 g) in ethanol (50 ml) was added and the mixture was stirred at room temperature for 24 hours. The solid which formed was recrystallised from ethanol to give the title product (mp 169°–171° C.).

EXAMPLES 52–56

The following compounds were prepared by the method described in Example 51

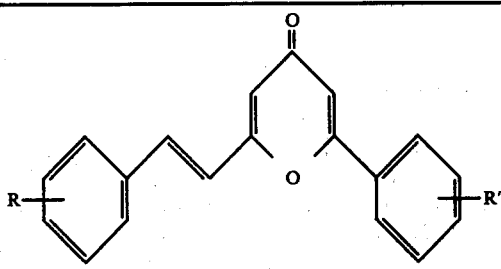

| Example | R | R' | mp °C. | Solvent of recrystallisation |
|---|---|---|---|---|
| 52 | 4-NO$_2$ | H | 246–249 (dec) | DMF-ethanol |
| 53 | 3-CF$_3$ | H | 149–151 | ethanol-water |
| 54 | 4-MeS | H | 167–168 | ethanol-water |
| 55 | 4-MeO | 4-Cl | 187–189 | ethanol |
| 56 | 4-Cl | 4-MeO | 171–172 | ethanol |

EXAMPLE 57

4-[2-(4-Oxo-6-phenyl-4H-pyran-2-yl)ethenyl]benzoic acid

2-Methyl-6-phenyl-4H-pyran-4-one (3.7 g) and 4-carboxybenzaldehyde (3.0 g) were added to a stirred solution of sodium ethoxide prepared by dissolving sodium (1.0 g) in ethanol (75 ml) and the mixture was heated under reflux for an hour, cooled and acidified with 2M hydrochloric acid (25 ml). The resulting solid was recrystallised from acetic acid and then from dimethylformamide-water to give the pale yellow title product (mp > 300° C.).

EXAMPLE 58

2-[2-(4-Hydroxyphenyl)ethenyl]-6-phenyl-4H-pyran-4-one

The ether linkage of 2-[2-(4-methoxyphenyl)ethenyl]-6-phenyl-4H-pyran-4-one was cleaved with boron tribromide as described in Example 47 to give the title product as orange needles (mp 198°–201° C.).

EXAMPLE 59

2-[2-(4-Acetamidophenyl)ethenyl]-6-phenyl-4H-pyran-4-one

A solution of concentrated hydrochloric acid (0.2 ml) in ethanol (20 ml) was added to a stirred refluxing suspension of 2-[2-(4-nitrophenyl)-ethenyl]-6-phenyl-4H-pyran-4-one (8.5 g) and iron powder (4.5 g) in ethanol (80 ml) and water (20 ml). The stirred mixture was heated under reflux for 5 hours, adding further concentrated hydrochloric acid (0.2 ml) after 2 hours. The hot mixture was filtered and the filtrate was evaporated under vacuum. The solid residue was crystallised from chloroform-petroleum ether 60°–80° C. to give 2-[2-(4-aminophenyl)ethenyl]-6-phenyl-4H-pyran-4-one (mp 192°–194° C.).

A stirred suspension of this compound (2.3 g) in acetic anhydride (0.75 ml) and toluene (50 ml) was heated under reflux for an hour. The mixture was cooled and the solid was crystallised from ethanol to give the title product (mp 271°–272° C. with decomposition).

EXAMPLE 60

2-[2-(4-Methylsulphonylphenyl)ethenyl]-6-phenyl-4H-pyran-4-one

A solution of 2-[2-(4-methylthiophenyl)ethenyl]-6-phenyl-4H-pyran-4-one (2.8 g) and m-chloroperoxybenzoic acid (3.6 g) in ethanol-free chloroform (45 ml) was stirred for 2 hours at room temperature. The white solid which formed was filtered off and the filtrate was washed with sodium bicarbonate solution, dried and evaporated. The residue was crystallised from ethanol-chloroform to give the title product (mp 239°–241° C.).

EXAMPLE 61

4-Oxo-6-(2-phenylethenyl)-4H-pyran-2-carboxylic acid

A solution of 2-methyl-2-(2-oxopropyl)-1,3-dioxolane (49 g) and diethyl oxalate (55 ml) in ethanol (50 ml) was added over 30 minutes to a stirred, cooled, solution of sodium ethoxide prepared by dissolving sodium (9.4 g) in ethanol (150 ml). The solution was stirred for 5 hours at room temperature and then acidified with 5M hydrochloric acid (200 ml) and then stirred for a further hour. The mixture was diluted with water (800 ml) and extracted with ethyl acetate, the extract was dried and evaporated and the residue was distilled under vacuum (bp 110°–120° C./0.2 mm). The distillate (53.8 g) was crystallised from ether-petroleum ether 40°–60° C. to give ethyl 6-methyl-4-oxo-4H-pyran-2-carboxylate (mp 35°–38° C.).

A solution of this ester (3.6 g) in ethanol (100 ml) was added to a solution of sodium ethoxide prepared by dissolving sodium (1.0 g) in ethanol (100 ml). Benzaldehyde (2.45 ml) was added and the stirred mixture was heated at 80°–90° C. for an hour, cooled, diluted with water (800 ml) and washed with ether. The aqueouse phase was acidified with 2M hydrochloric acid and extracted with ethyl acetate. The extract was dried and evaporated and the solid residue was recrystallised from dimethylformamide-water to give the title product (mp 227°–228° C. with decomposition).

EXAMPLE 62

6-[2-(4-Methoxyphenyl)ethenyl]-4-oxo-4H-pyran-2-carboxylic acid

The above compound was prepared as described in Example 61 (mp 232°–234° C. with decomposition).

EXAMPLE 63

6-[2-(4-Hydroxyphenyl)ethenyl]-4-oxo-4H-pyran-2-carboxylic acid

Boron tribromide (2.5 ml) was added to a stirred suspension of 6-[2-(4-methoxyphenyl)ethenyl]-4-oxo-4H-pyran-2-carboxylic acid (1.4 g) in methylene chloride (140 ml) and the mixture was stirred for 3 hours at room temperature and 1 hour under reflux. Water (30 ml) was added to the stirred mixture and the solid product was crystallised from ethanol-water to give the title product (mp 256° C. with decomposition).

EXAMPLE 64

Ethyl 5-bromo-6-(4-chlorophenyl)-2,4-dioxo-5-hexenoate

The above compound was prepared by the method described in Example 1 (mp 79°–81° C.).

EXAMPLE 65

Ethyl 6-(4-chlorophenyl)-4-oxo-4H-pyran-2-carboxylate

The above compound was prepared from ethyl 5-bromo-6-(4-chlorophenyl)-2,4-dioxo-5-hexenoate (Example 64) by the method described in Example 8 and was identical (mp, IR, NMR) to the product of Example 12.

EXAMPLE 66

Ethyl 6-(4-chlorophenyl)-2,4,6-trioxohexanoate

A solution of 1-(4-chlorophenyl)-1,3-butanedione (0.6 g) and diethyl oxalate (0.83 ml) in 1,2-dimethoxyethane (2 ml) was added to a stirred suspension of sodium hydride (0.44 g, 50% dispersion in mineral oil, washed with petrol 40°–60° C.) in 1,2-dimethoxyethane (5 ml) under nitrogen. The stirred mixture was heated under reflux for 1 hour, cooled and acidified with 2M hydrochloric acid (10 ml). The brown solid which formed was recrystallised from ethanol-water to give the title product (mp 93°–94° C.).

EXAMPLE 67

Ethyl 6-(4-chlorophenyl)-4-oxo-4H-pyran-2-carboxylate

A solution of ethyl 6-(4-chlorophenyl)-2,4,6-trioxohexanoate (0.26 g) in cold concentrated sulphuric acid (3 ml) was stirred for 3 hours at 0°–5° C. then poured on to ice (10 g). The solid product was recrystallised from ethanol-water to give the title product identical (mp, IR and NMR, and thin-layer chromatography) with the product described in Example 12.

EXAMPLE 68

6-(4-Chlorophenyl)-4-oxo-4H-pyran-2-carboxylic acid

A solution of ethyl 6-(4-chlorophenyl)-2,4,6-trioxohexanoate (0.30 g) in dioxan (2 ml) and concentrated hydrochloric acid (2 ml) was heated on a steam bath for 2 hours. The pale solid which formed was recrystallised from ethanol to give the title product identical (mp, IR and NMR, and thin-layer chromatography) with the product described in Example 24.

EXAMPLE 69

Ethyl 6-phenyl-2,4,6-trioxohexanoate

This compound was prepared by a method similar to that described in Example 66 (mp 105° C.).

EXAMPLE 70

Methyl 6-phenyl-2,4,6-trioxohexanoate

This compound was prepared by a method similar to that described in Example 66 using dimethyl oxalate in dimethylformamide solution (mp 107°–109° C.).

EXAMPLE 71

3-Bromo-4-oxo-6-phenyl-4H-pyran-2-carboxylic acid

A solution of bromine (10.25 ml, 0.198 mol) in chloroform (50 ml) was added dropwise over 30 minutes to a stirred solution of ethyl 6-phenyl-2,4,6-trioxohexanoate (52.0 g) in chloroform (400 ml) at −10° to −20° C. The pale solution was stirred for a further 3 hours without cooling, washed with water and evaporated. The residual solid was recrystallised from ethanol-water to give ethyl 3-bromo-4-oxo-6-phenyl-4H-pyran-2-carboxylate (mp 135° C.). This ester was hydrolysed as in Example 33 to give the title product (mp 247° C. with decomposition).

EXAMPLE 72

3-Bromo-6-(4-methylphenyl)-4-oxo-4H-pyran-2-carboxylic acid

Ethyl 6-(4-methylphenyl)-2,4,6-trioxohexanoate (mp 76° C.) was prepared by the method described in Example 66 and brominated and cyclised as described in Example 71 to give ethyl 3-bromo-6-(4-methylphenyl)-4-oxo-4H-pyran-2-carboxylate (mp 144° C.). This ester was hydrolysed by the method described in Example 33 to give the title product (mp 202°–204° C. with decomposition).

EXAMPLE 73

3-Chloro-4-oxo-6-phenyl-4H-pyran-2-carboxylic acid

Trifluoromethane sulphonyl chloride (3.95 ml) was added over 10 minutes to a stirred solution of ethyl 6-phenyl-2,4,6-trioxohexanoate (8.1 g) and triethylamine (6.5 ml) in dichloromethane (100 ml) at 0° to 5° C. The solution was stirred for 2 hours at 0° to 5° C., then made acidic by passing in hydrogen chloride gas. The mixture was stirred for 3 hours at room temperature, washed with water and evaporated to a brown oil which crystallised from ethanol-water. The product was recrystallised from ethanol-water and from ethyl acetate-petroleum ether 60°–80° C. to give ethyl 3-chloro-4-oxo-6-phenyl-4H-pyran-2-carboxylate (mp 121° C.).

This ethyl ester was hydrolysed as described in Example 33 to give the title product (mp 250° C. with decomposition).

EXAMPLE 74

Methyl 3-bromo-4-oxo-6-phenyl-4H-pyran-2-carboxylate

The above compound was prepared by a method similar to that described in Example 71 using dichloromethane as solvent (mp 130° C.).

EXAMPLE 75

3-Bromo-4-oxo-6-phenyl-4H-pyran-2-carboxylic acid

Methyl 3-bromo-4-oxo-6-phenyl-4H-pyran-2-carboxylate (587 g) was added to a stirred solution of dry sodium iodide (315 g) in dry methyl ethyl ketone (8 l). The solution was heated under reflux for 5 minutes, then pyridine (152 ml) was added and heating was continued for 3½ hours. The mixture was cooled, the solid product was dissolved in water (2 l) and the solution was washed with dichloromethane and filtered. The filtrate was diluted to 10 l and acidified with 5M hydrochloric acid (760 ml) to precipitate the title product (mp 247° C. with decomposition).

EXAMPLE 76

6-(1-Naphthalenyl)-4-oxo-4H-pyran-2-carboxylic acid

A solution of 1-(1-naphthalenyl)-1,3-butanedione (5.3 g) and diethyl oxalate (6.75 ml) in 1,2-dimethoxyethane (10 ml) was added dropwise to a stirred suspension of sodium hydride (3.6 g, 50% dispersion in mineral oil, washed with petrol 40°-60° C.) in 1,2-dimethoxyethane (40 ml) under nitrogen. The stirred mixture was heated under reflux for 5 minutes, cooled, acidified with 2M hydrochloric acid (50 ml), diluted with water (50 ml) and filtered. The filtrate was extracted with ethyl acetate and the extract was dried and evaporated to yield ethyl 6-(1-naphthalenyl)-2,4,6-trioxohexanoate as a dark oil.

This crude ester was dissolved in dioxan (50 ml) and concentrated hydrochloric acid (50 ml), and the solution was heated under reflux for 1½ hours then concentrated under vacuum to give a brown solid. The solid was recrystallised from ethanol and from ethanol-water to give the title product (mp 248°-249° C. with decomposition).

EXAMPLE 77

6-(4-Benzyloxyphenyl)-4-oxo-4H-pyran-2-carboxylic acid

A mixture of ethyl 6-(4-hydroxyphenyl)-4-oxo-4H-pyran-2-carboxylate (3.3 g), anhydrous potassium carbonate (3.5 g) and benzyl bromide (2.0 ml) in dry dimethylformamide (30 ml) was stirred at room temperature for 20 hours. The mixture was filtered and the filtrate was cooled and acidified with 0.4M hydrochloric acid (100 ml). The solid product was recrystallised from ethanol-water to give a mixture of ethyl and benzyl 6-(4-benzyloxyphenyl)-4-oxo-4H-pyran-2-carboxylate.

A solution of this mixed ester (1.1 g) and dry lithium iodide (2.0 g) in dry dimethylformamide (30 ml) was heated at 165°-170° C. under nitrogen for 6 hours, cooled and diluted with 1M hydrochloric acid (60 ml). The solid product was recrystallised from ethanol to give the title product (mp 235° C.).

EXAMPLE 78

6-(4-Methylsulphonylphenyl)-4-oxo-4H-pyran-2-carboxylic acid

Ethyl 6-(4-methylsulphonylphenyl)-4-oxo-4H-pyran-2-carboxylate (mp 176°-179° C.) was prepared by oxidation of ethyl 6-(4-methylthiophenyl)-4-oxo-4H-pyran-2-carboxylate using the method described in Example 60.

This ethyl ester was hydrolysed by the method described in Example 23 to give the title product (mp 269°-271° C. with decomposition).

EXAMPLE 79

N-Methyl-6-(4-methylsulphonylphenyl)-4-oxo-4H-pyran-2-carboxamide

This compound was prepared from ethyl 6-(4-methylsulphonylphenyl)-4-oxo-4H-pyran-2-carboxylate (see Example 78) by the method described in Example 37 (mp 262°-266° C.).

EXAMPLE 80

6-(3-Acetamidophenyl)-4-oxo-4H-pyran-2-carboxylic acid

The above compound was prepared by the method described in Example 33 (mp 245°-248° C.).

EXAMPLE 81

Acetoxymethyl 3-bromo-4-oxo-6-phenyl-4H-pyran-2-carboxylate

Chloromethyl acetate (2.2 ml) was added to a stirred solution of 3-bromo-4-oxo-6-phenyl-4H-pyran-2-carboxylic acid (5.9 g) and triethylamine (2.9 ml) in dry DMF (40 ml). The solution was heated at 70°-80° C. for 3 hours, then poured on to ice-water and extracted with ethyl acetate. The extract was washed with sodium bicarbonate solution, dried and evaporated, and the residue was crystallised from ethanol-water. The crude product was purified by chromatography on silica-gel and recrystallisation from ethyl acetate-petroleum ether 60°-80° C. gave the title product as white needles (mp 121° C.).

EXAMPLE 82

Methylthiomethyl 3-bromo-4-oxo-6-phenyl-4H-pyran-2-carboxylate.

This compound was prepared by the method described in Example 81 (mp 148° C.).

EXAMPLE 83

Methylsulphinylmethyl 3-bromo-4-oxo-6-phenyl-4H-pyran-2-carboxylate

A solution of methylthiomethyl 3-bromo-4-oxo-6-phenyl-4H-pyran-2-carboxylate (0.36 g) and m-chloroperoxybenzoic acid (0.22 g, 80% pure) in chloroform (5 ml) was stirred for 4 hours at room temperature, filtered, washed with sodium bicarbonate solution, and evaporated. The residue was recrystallised from ethyl acetate-petroleum ether 60°-80° C. to give the title product (mp 159° C.).

EXAMPLE 84

Methylsulphonylmethyl 3-bromo-4-oxo-6-phenyl-4H-pyran-2-carboxylate.

A stirred solution of methylthiomethyl 3-bromo-4-oxo-6-phenyl-4H-pyran-2-carboxylate (0.36 g) and m-chloroperoxybenzoic acid (0.44 g, 80% pure) in chloroform (5 ml) was heated at 60° C. for 1 hour. The mixture was diluted with chloroform (50 ml) to dissolve all the solid and the solution was washed with sodium bicarbonate solution, dried and evaporated. The residue was recrystallised from chloroform-petroleum ether 60°-80° C. to give the title product (mp 192° C.).

EXAMPLE 85

5-Methyl-4-oxo-6-phenyl-4H-pyran-2-carboxylic acid

Ethyl 5-methyl-6-phenyl-2,4,6-trioxohexanoate was prepared from 2-methyl-1-phenyl-1,3-butanedione by the method described in Example 66. The crude oily hexanoate was cyclised as described in Example 68 to give the title product (mp 218° C.).

The following formulations can be prepared using as active ingredient the compound 3-bromo-4-oxo-6-phenyl-4H-pyran-2-carboxylic acid and similar formulations prepared from other solid compounds can be made.

EXAMPLE 86

Tablets each containing 50 mg of active ingredient were made up as follows:

| | |
|---|---|
| Active ingredient | 50 mg |
| Starch | 200 mg |
| Lactose | 200 mg |
| Polyvinylpyrrolidone | 20 mg |
| (as 10% solution in water) | |
| Sodium starch glycolate | 20 mg |
| Magnesium stearate | 10 mg |
| Total | 500 mg |

The starch, lactose and active ingredient were passed through a sieve and thoroughly mixed. The solution of polyvinylpyrrolidone was mixed with the resultant mixture and the combination passed through a No. 12 mesh B.S. sieve. The granules so produced were dried at approximately 55° C. and passed through a No. 16 mesh B.S. sieve. The magnesium stearate and sodium starch glycolate, previously passed through a No. 60 mesh B.S. sieve, were then added to the granules which, after mixing, were compressed on a tablet machine to yield tablets each weighing 500 mg.

EXAMPLE 87

Capsules each containing 50 mg of medicament were made as follows:

| | |
|---|---|
| Active ingredient | 50 mg |
| Starch | 42 mg |
| Lactose | 45 mg |
| Magnesium stearate | 3 mg |
| Total | 140 mg |

The lactose, starch, magnesium stearate and active ingredient were passed through a No. 44 mesh B.S. sieve and filled into hard gelatin capsules in 140 mg quantities.

EXAMPLE 88

Suppositories each containing 50 mg of active ingredient were made as follows:

Active ingredient: 50 mg

Saturated fatty acid glycerides to: 2,000 mg

The active ingredient was passed through a No. 60 mesh B.S. sieve and suspended in the saturated fatty acid glycerides previously melted using the minimum heat necessary. The mixture was then poured into a suppository mould of nominal 2 g capacity and allowed to cool.

We claim:

1. A pharmaceutical formulation in unit dosage form adapted for administration to treat an immediate hypersensitivity condition of the type represented by asthma which comprises per dosage unit an effective amount of a compound of the formula:

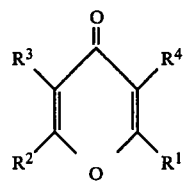

in which $R^1$ is $COOR^5$, $CONHR^5$, cyano, 5-tetrazolyl or $R^6$, where $R^5$ is hydrogen or $C_{1-8}$ alkyl and $R^6$ is phenyl or naphthyl, the phenyl or naphthyl group being optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$ and $SR^5$; $R^2$ is $R^6$ or $-CH=CH-R^6$ when $R^1$ is $COOR^5$, $CONHR^5$, cyano or 5-tetrazolyl, or $R^2$ is $-CH=CH-R^6$ when $R^1$ is $R^6$; $R^3$ is hydrogen, $C_{1-6}$ alkyl, halogen, hydroxy or $-OCH_2R^6$; and $R^4$ is hydrogen, $C_{1-6}$ alkyl or halogen; or a pharmaceutically-acceptable salt thereof; associated with a pharmaceutically-acceptable carrier therefor; provided that:

(i) when $R^3$ is hydrogen, $R^4$ is hydrogen or methyl, and $R^1$ is $COOR^5$ or $CONHR^5$ where $R^5$ is hydrogen, methyl or ethyl, $R^2$ is not phenyl, (ii) when $R^3$ and $R^4$ are both hydrogen, and $R^1$ is $COOR^5$, where $R^5$ is methyl, $R^2$ is not 2-methoxyphenyl or 4-methoxyphenyl, (iii) when $R^3$ and $R^4$ are both hydrogen, and $R^1$ is $COOR^5$ where $R^5$ is ethyl, $R^2$ is not 3,4-dimethoxyphenyl, and (iv) when $R^3$ and $R^4$ are both hydrogen, and $R^1$ is phenyl or 4-methoxyphenyl, $R^2$ is not styryl or 4-methoxystyryl.

2. A pharmaceutical formulation in unit dosage form adapted for administration to treat an immediate hypersensitivity condition of the type represented by asthma which comprises per dosage unit an effective amount of a compound of the formula

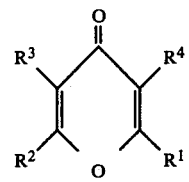

wherein $R^1$ is $COOR^5$ where $R^5$ is hydrogen or $C_{1-8}$ alkyl; $R^2$ is phenyl optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$, or $SR^5$; $R^3$ is hydrogen and $R^4$ is halogen or a pharmaceutically-acceptable salt thereof, associated with a pharmaceutically-acceptable carrier therefor.

3. A method of treating an animal, including a human, susceptible to or suffering from an immediate hypersensitivity condition of the type represented by asthma, which comprises administering an effective amount of a compound of the formula

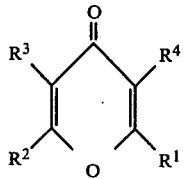

in which $R^1$ is $COOR^5$, $CONHR^5$, cyano, 5-tetrazolyl or $R^6$, where $R^5$ is hydrogen or $C_{1-8}$ alkyl and $R^6$ is phenyl or naphthyl, the phenyl or naphthyl group being optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$ and $SR^5$; $R^2$ is $R^6$ or $-CH=CH-R^6$ when $R^1$ is $COOR^5$, $CONHR^5$, cyano or 5-tetrazolyl, or $R^2$ is $-CH=CH-R^6$ when $R^1$ is $R^6$; $R^3$ is hydrogen, $C_{1-6}$ alkyl, halogen, hydroxy or $-OCH_2R^6$; and $R^4$ is hydrogen, $C_{1-6}$ alkyl or halogen; or a pharmaceutically-acceptable salt therefor.

4. A method of treating an animal, including a human, susceptible to or suffering from an immediate hypersensitivity condition of the type represented by asthma, which comprises administering an effective amount of a compound as defined in claim 3 wherein $R^6$ is phenyl optionally substituted by one or more groups selected from halogen, $C_{1-6}$ alkyl, $C_{1-4}$ alkoxy, hydroxy, benzyloxy, nitro, trifluoromethyl, carboxyl, $C_{1-4}$ alkylsulphinyl, $C_{1-4}$ alkylsulphonyl, $N(R^5)_2$, $NHCOR^5$, or $SR^5$.

5. The formulation of claim 2 in which the compound is 3-bromo-4-oxo-6-phenyl-4H-pyran-2-carboxylic acid.

6. The method of claim 4 in which the compound is 3-bromo-4-oxo-6-phenyl-4H-pyran-2-carboxylic acid.

* * * * *